(12) United States Patent
Spreitzer et al.

(10) Patent No.: US 7,402,717 B2
(45) Date of Patent: Jul. 22, 2008

(54) METHOD FOR PRODUCING OLEFIN-SUBSTITUTED AROMATIC OR HETEROAROMATIC COMPOUNDS

(75) Inventors: Hubert Spreitzer, Viernheim (DE); Philipp Stössel, Frankfurt (DE); Heinrich Becker, Glashütten (DE)

(73) Assignee: Merck Patent GmbH (DE)

( * ) Notice: Subject to any disclaimer, the term of this patent is extended or adjusted under 35 U.S.C. 154(b) by 526 days.

(21) Appl. No.: 10/343,291

(22) PCT Filed: Aug. 1, 2001

(86) PCT No.: PCT/EP01/09175

§ 371 (c)(1),
(2), (4) Date: Sep. 25, 2003

(87) PCT Pub. No.: WO02/10093

PCT Pub. Date: Feb. 7, 2002

(65) Prior Publication Data

US 2004/0254388 A1  Dec. 16, 2004

(30) Foreign Application Priority Data

Aug. 1, 2000  (DE) ................................ 100 37 390

(51) Int. Cl.
*C07C 2/72* (2006.01)
*C07C 2/64* (2006.01)
*C07C 2/68* (2006.01)

(52) U.S. Cl. .................. 585/467; 585/428; 585/446
(58) Field of Classification Search ................. 570/101, 570/123, 138
See application file for complete search history.

(56) References Cited

U.S. PATENT DOCUMENTS

| 4,400,544 | A | | 8/1983 | Takehira et al. ............. 568/360 |
| 5,703,269 | A | * | 12/1997 | Herrmann et al. ............. 560/19 |
| 6,392,111 | B1 | * | 5/2002 | Reetz et al. ................. 585/436 |

FOREIGN PATENT DOCUMENTS

| DE | 19843012 | 3/2000 |
| WO | 98/42644 | 10/1998 |

OTHER PUBLICATIONS

Mitra et al., Journal of the Indian Chemical Society (1997), 74(2), 146-147 (Mitra).*
<http://www.organic-chemistry.org/namedreactions/heck-reaction.shtm>, retrieved Mar. 28, 2007.*
Bozell, J.J., et al., "Bimetallic Catalysis. A New Method for the Activation of Chloroarenes toward Palladium-Catalyzed Coupling with Olefins", *J. Am. Chem. Soc.*, 1988, vol. 110, pp. 2655-2657.
Mitra, et al., "Palladium in Organic Synthesis. Part-V. Palladium-catalysed Insertion of Chloroarenes to the Olefins using Cobalt as Co-catalyst", *J. Indian Chem., Soc.*, vol. 74, pp. 146-147 (1997).
Hansen, et al., "Regioselective Heck Couplings of $\alpha,\beta$-Unsaturated Tosylates and Mesylates with Electron-Rich Olefins", *American Chemical Society, Organic Letters*, vol. 7, No. 25, pp. 5585-5587 (2005).

* cited by examiner

*Primary Examiner*—Karl J Puttlitz
(74) *Attorney, Agent, or Firm*—Connolly Bove Lodge & Hutz LLP

(57) ABSTRACT

Both low molecular weight and high molecular weight aromatic and heteroaromatic compounds which are substituted by olefins play an important role in industry, for instance as assistants and additives in cosmetic preparations, for example in sunscreens, various fine and electronics chemicals, and precursors for pharmaceuticals and agrochemicals. Also, particularly in the rapidly growing field of organic semiconductors (for example applications in organic or polymeric light emitting diodes, organic solar cells, organic ICs), precisely these compounds are of outstanding significance.

The present invention relates to a process for preparing such olefin-substituted aromatics or heteroaromatics by reacting a functional aryl or heteroaryl compound with an olefin derivative which has at least one hydrogen atom on the double bond in the presence of a simple palladium compound, optionally in the presence of a nitrogen additive, and of a base in a solvent, to form a C—C bond and formally cleave off the functional group of the aryl or heteroaryl derivative and a hydrogen atom of the olefin compound, characterized by the presence of at least one metal additive other than palladium.

18 Claims, No Drawings

METHOD FOR PRODUCING OLEFIN-SUBSTITUTED AROMATIC OR HETEROAROMATIC COMPOUNDS

Both low molecular weight and high molecular weight aromatic and heteroaromatic compounds which are substituted by olefins play an important role in industry, for instance as assistants and additives in cosmetic preparations, for example in sunscreens, various fine and electronics chemicals, and precursors for pharmaceuticals and agrochemicals, to name just a few fields of application. Also, particularly in the rapidly growing field of organic semiconductors (for example applications in organic or polymeric light emitting diodes, organic solar cells, organic ICs), precisely these compounds are of outstanding significance.

For the preparation, highly varying alternatives are known, which, however, do not in all cases offer a satisfactory solution, for example economically or ecologically. In many processes, coproducts occur which have to be removed and disposed of in a costly and inconvenient manner.

From the synthetic aspect, direct linking of an aromatic/heteroaromatic derivative with an olefin derivative is frequently a favorable starting point.

In this case, the Heck reaction (cf. R. F. Heck, Compr. Org. Synth. 1991, 883) is a suitable choice (cf. FIG. 1).

FIG. 1. General reaction equation of a HECK reaction.

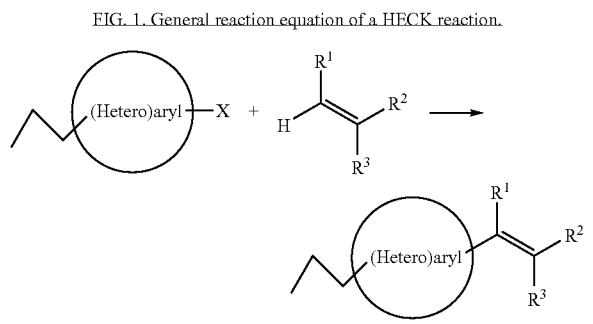

Although this reaction has already been researched for several years, there is still a shortage of industrially suitable processes. The first attempts in this direction were made a short time ago by the research group of Prof. Reetz. Since this work (cf. below: WO98/42644, DE 198 43 012) represents the prior art closest to the present application, it is hereby incorporated by way of reference into the application. In particular, the repetition of the comprehensive descriptions of the general prior art with regard to HECK reactions is dispensed with.

In WO98/42644, Reetz was able to show that the reaction of an appropriate aromatic or heteroaromatic compound with an appropriate olefin in the presence of a palladium catalyst, a tetraarylphosphonium salt, a dipolar aprotic solvent, a base and optionally an additive (which is an α- or β-amino acid derivative) proceeds with a distinctly better yield than can be inferred from the prior art cited in the abovementioned application. For instance, it is possible under industrially suitable conditions to achieve degrees of conversion of up to 98% and coupling selectivities of likewise up to approx. 98% (see example 24 of the abovementioned application).

For the purposes of this application, selectivity means that the desired stereoselectivity is achieved. In the case of the reactions of styrene of Reetz, this is usually-characterized by quoting the three possible products (trans product, cis product and 2-linked product). In the case of certain olefins, a selectivity of 100% is achieved when there is only one way of linking.

In a further improvement (DE 198 43 012), Reetz was able to show that for certain aryl/heteroaryl derivatives an even simpler process leads to very good results: when the tetraarylphosphonium salts are dispensed with and α- or β-amino acid derivatives, preferably dimethylglycine, are consistently used instead, industrially utilizable yields of up to 99% and selectivities of up to approx. 99% (cf. in particular examples 39 to 45 in DE 198 43 012) are achieved. However, it is unsatisfactory that a very high conversion does not result at the same time in very high selectivities. An advantage of the latter process is in any case the dispensation with phosphine/phosphonium components which otherwise have to be removed from the product, sometimes with difficulty.

For many simple reactions, the conditions found and published by Reetz could suffice to develop economically viable processes. However, if the problem arises of reacting a multifunctional compound (cf. FIG. 2) or even constructing a polymerization (cf. FIG. 3) in this way, even degrees of conversion of up to 99% (with selectivities which would then be distinctly below 100%) may lead to distinct problems.

FIG. 2. Example of the conversion of a multifunctional compound.

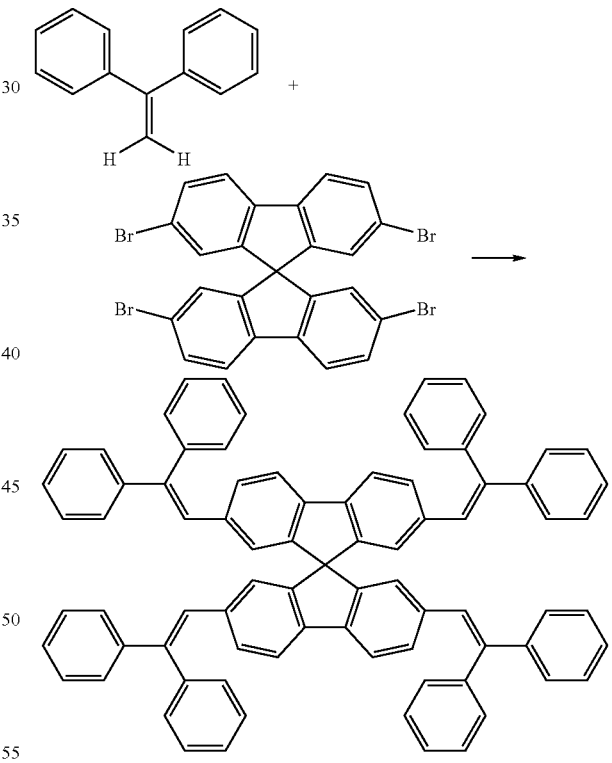

FIG. 3. Example of the conversion to a polymer.

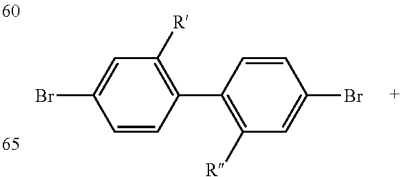

-continued

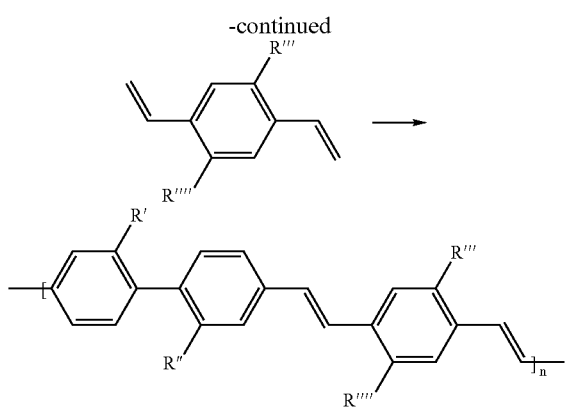

For instance, in the case of the example of FIG. 2, a conversion rate (per single step) of, for example, 99%, assuming a SELECTIVITY in each case of 99% (i.e. per single addition 0.99×0.99=98% yield of the desired substitution pattern), leads to an overall yield of approx. 92%. However, this relatively high-yield is still unsatisfactory in view of the purity requirements of +99.9% in, for example, electronic applications, since the purification is very costly and inconvenient owing to the high number of different secondary components. It is therefore clear that the use of the Reetz processes is unsatisfactory for this purpose (cf. also examples 4 to 7 in this connection).

A similar problem applies to the polymerization example in FIG. 3. In theory, a polycondensation at a conversion rate of 99% leads to a maximum degree of polymerization of 100. Furthermore, a selectivity of (distinctly) less than 100% leads either to defects in the main polymer chain or to further chain terminations. In reality, the degree of polymerization should therefore rather be distinctly below 100. This, together with the possible main chain defects, may prove to be a serious problem for many applications (for example use in polymeric light emitting diodes or in organic ICs).

Since it is now obvious that the above-illustrated HECK reaction is on the one hand very suitable in principle for preparing appropriate olefin-substituted aromatics or heteroaromatics, but on the other hand the existing methods are still unsatisfactory for certain requirements, there is a definite need for improvement on the above-detailed prior art.

It has now surprisingly been found that the HECK reaction illustrated above in the prior art can be decisively improved by a clearly defined variation, so that the problems illustrated in the description of the FIGS. 2 and 3 can be solved. For example (cf. the examples), products of conversion×selectivity for single steps in the order of magnitude of more than 99.5% have been achieved which, even in the reaction of multifunctional compounds (similar to FIG. 2), leads to crude yields/purities of over 98% and degrees of polymerization from a few hundred to 1000.

For the purposes of this application, multifunctional is intended to mean that a compound has a plurality of (for example two, three, four, five, etc.) identical units or units with identical functions which all react in the same way to give a product molecule in the appropriate reaction (in this case, HECK reaction). The reaction of multifunctional compounds refers initially to the reaction of a multifunctional compound with a plurality of monofunctional compounds to give a defined "low molecular weight" compound. When, in contrast, (at least) two different multifunctional compounds are reacted with each other, the product will have polymeric character, as is shown in FIG. 3 for the reaction of two bifunctional compounds. This also expressly represents a HECK reaction for the purposes of this invention.

The novel process according to the invention is the reaction of a functional aryl or heteroaryl compound with an olefin derivative which has at least one hydrogen atom on the double bond in the presence of a simple palladium compound, optionally in the presence of a nitrogen additive, and of a base in a solvent, to form a C—C bond and formally cleave off the functional group of the aryl or heteroaryl derivative and a hydrogen atom of the olefin compound, characterized by the presence of at least one metal additive other than palladium.

Preference is given to the abovementioned process when a nitrogen additive is actually used in addition to the metal additive.

Very particular preference is given to aminocarboxylic acids and their derivatives, such as dimethylglycine, 4-dimethylaminobutyric acid and 3-indolylacetic acid.

The metal additives are metals, alloys, compounds, salts or chalcogenides of the d transition groups of the Periodic Table.

Preference is given to transition metals from the vanadium group to the zinc group, more preferably the corresponding additives comprising the metals iron, cobalt, nickel, ruthenium, rhodium, osmium, iridium or platinum, even more preferably iron, nickel or cobalt, most preferably iron.

Salts of the metals, such as halides, sulfates, acetates or other carboxylates, may be used. It is further possible to use oxides or complexes (for example metallocenes). However, it is also in accordance with the invention to add the metals directly or as alloys to the reaction mixture, for example as metal dust or powder. In the case of the particularly preferred use of iron, it is also possible to use iron ores, different forms of steel or cast iron (for example powders or waddings) or similar commercial forms.

Aryl or heteroaryl compounds are monofunctional aromatics or heteroaromatics which have from 4 to 40 carbon atoms and may be substituted by one or else more than one linear, branched or cyclic alkyl or alkoxy radical having from 1 to 20 carbon atoms in which in turn one or more $CH_2$ groups which are not adjacent may be replaced by O, S, C=O or a carboxyl group, unsubstituted C-4 to C-20 aryl or heteroaryl radicals, fluorine, cyano, nitro or sulfonic acid derivatives, or else be unsubstituted. Reference is also explicitly made in this connection to the above-cited applications of Reetz et al. and the aryl and heteroaryl systems listed there. Simple compounds which may be used with preference are the appropriate functionalized derivatives of benzene, naphthalene, anthracene, pyrene, biphenyl, fluorene, spiro-9,9'-bifluorene, phenanthrene, triptycene, pyridine, furan, thiophene, pyrrole, quinoline, quinoxaline, pyrimidine and pyrazine.

Appropriate (in the sense of the above text) multifunctional compounds are also explicitly incorporated, and likewise the oligomers having functional aryl or heteroaryl ends resulting from a polymerization.

The functional group in the functional aryl or heteroaryl compounds is a reactive leaving group suitable for the reaction described. This is preferably chlorine, bromine, iodine, methylsulfonate, tosylate, triflate, nonaflate or a diazonium salt group.

Similarly to the descriptions in the Reetz applications cited, the olefin derivative has a maximum of three substituents on the double bond. The substituents may be similar to those described for the aryl or heteroaryl compound, or else be the aldehyde, carboxylic acid derivative groups, or else further groups as described in Reetz.

Simple compounds which may be used with preference are ethylene, propylene, acrylic acid derivatives, methacrylic acid derivatives, styrene derivatives, diphenylethene derivatives, vinyl ethers and vinyl acetate.

Appropriate (in the sense of the above text) multifunctional compounds are also explicitly incorporated, and likewise the oligomers having olefinic ends resulting from a polymerization.

For the purposes of the applications of Reetz et al., a simple palladium compound is a palladium-II compound, for example a palladium-II halide, palladium-II acetate, or a simple complex which can be derived from them, or else supported or unsupported, disperse or colloidal metallic palladium, or else further palladium-(0) compounds such as $Pd_2 dba_3$ and the like.

Furthermore, the following Pd compounds can also be used:

palladium ketonates, palladium acetylacetonates, nitrile palladium halides, olefinpalladium halides, allylpalladium halides and palladium biscarboxylates.

Similarly to the applications of Reetz et al., bases are used, preferably hydrogencarbonates, carbonates, acetates and other carboxylates, such as propionates, formates and benzoates.

A variant may also involve using the metal additive at the same time as part of the base, for example by (concomitantly) using iron-(II) acetate or nickel-(II) carbonate.

Likewise similarly to the application of Reetz et al., solvents are used, i.e. preferably dipolar aprotic solvents, more preferably dimethylacetamide, dimethylformamide or N-methylpyrrolidinone; optionally also protic solvents such as methanol or ethylene glycol.

The nitrogen additive which is optionally concomitantly to be used with preference is either, likewise similarly to the descriptions of Reetz et al., an α- or β-aminocarboxylic acid or derivatives derived therefrom, for example the dimethylglycine described as preferred by Reetz, or else longer aminocarboxylic acids such as γ- or δ-aminocarboxylic acids and their derivatives, for example 4-dimethylaminobutyric acid or 3-indolylacetic acid.

In the process according to the invention, the palladium catalyst is generally used in an amount of from 0.001 to 10 mol % (of palladium) based on the amount of C—C bonds to be formed. Preference is given to the range from 0.01% to 5%, particular preference to the range from 0.05% to 2.5%.

The amount of the metal additive relative to the palladium catalyst is relatively uncritical, but is generally between 1 and 500 mol % (based on the amount of palladium!), preferably between 5 and 200 mol %, more preferably between 10 and 100 mol %.

Between 0.5 and 10 equivalents, based on the amount of C—C bonds to be formed, are generally used. Preference is given to the range between 0.8 and 5 equivalents, particular preference between 0.8 and 3 equivalents.

It will be appreciated that the concentration of the reactants in the solvent depends on the particular reaction. However, the reaction preferably takes place in the range from 0.1 mol/l up to 5 mol/l, based on the amount of C—C bonds to be formed. However, it is also possible to use one of the reactants (for example the olefin component) in excess directly as solvent.

The reaction according to the invention is thermally activated and therefore generally takes place in a temperature range above room temperature, preferably from 40 to 200° C., more preferably from 60 to 180° C., most preferably from 100 to 160° C.

Particular preference is given to the process according to the invention when the palladium compound used is palladium acetate or palladium chloride, and the metal additive used is an iron-II or iron-III salt such as iron chloride.

Preference is given to using the process according to the invention for reacting multifunctional aryl or heteroaryl compounds with olefins which react monofunctionally.

Preference is likewise given to using the process according to the invention for reacting monofunctional aryl or heteroaryl compounds with olefins or compounds which have a plurality of monofunctional olefinic ends and react multifunctionally.

Preference is further given to using the process according to the invention for preparing polymers by reacting bifunctional aryl or heteroaryl compounds with bifunctional olefin derivatives (possibly bisolefins similar to the example in FIG. 3).

This preference results simply from the high rate of reaction and selectivity of the process according to the invention.

Despite this preference for multiple reactions, it will be appreciated that the process according to the invention also achieves outstanding results in single reactions, so that the process according to the invention may also be used here with preference.

The invention described is illustrated by the examples which follow, but is in no way restricted to these, but may of course instead be applied simply by those skilled in the art to the above-listed systems and those described in the literature cited.

EXAMPLE 1

632.0 mg (1.0 mmol) of 2,2',7,7'-tetrabromospirobifluorene, 9.0 mg (0.04 mmol) of palladium(II) acetate, 82.5 mg (0.8 mmol) of N,N-dimethylglycine and 1008.1 mg (12.0 mmol) of sodium hydrogencarbonate were weighed into a reaction vessel equipped with a septum and pressure equalizing valve. In addition, the specified amount of the metal additive (see table 1) was added by weighing. The reaction vessel was evacuated three times and purged with argon. 1081 mg, corresponding to 1059 µl (6.0 mmol), of 1,1-diphenylethene and 5.0 ml of degassed N-methylpyrrolidinone were then added with the aid of a syringe.

The reaction vessel was closed and the mixture stirred at the specified temperature for 18 h.

After 18 hours, 25 µl samples were withdrawn in each case, diluted with 10 ml of tetrahydrofuran and 10 ml of methanol, and filtered via a syringe filter. The content of the Heck product was determined by HPLC.

TABLE 1

| Example No. | Metal additive [mol %], based on palladium used | Reaction temperature | Yield of Heck product in the reaction mixture |
|---|---|---|---|
| 1.1 | ---none--- | 140° C. | 94.1% |
| 1.2 | vanadium(III) acetylacetonate 20 mol % | 140° C. | 97.2% |
| 1.3 | chromium(III) acetylacetonate 20 mol % | 140° C. | 96.8% |
| 1.4 | chromium(III) acetylacetonate 200 mol % | 140° C. | 96.8% |
| 1.5 | iron(II) acetate 20 mol % | 140° C. | 97.9% |
| 1.6 | iron(III) acetylacetonate 10 mol % | 140° C. | 97.7% |
| 1.7 | iron(III) acetylacetonate 100 mol % | 140° C. | 97.7% |
| 1.8 | iron(III) chloride hexahydrate 10 mol % | 140° C. | 98.1% |

TABLE 1-continued

| Example No. | Metal additive [mol %], based on palladium used | Reaction temperature | Yield of Heck product in the reaction mixture |
|---|---|---|---|
| 1.9 | iron(III) chloride hexahydrate 20 mol % | 140° C. | 98.4% |
| 1.9 | iron(III) chloride hexahydrate 200 mol % | 140° C. | 98.0% |
| 1.10 | nickel(II) chloride hexahydrate 20 mol % | 140° C. | 97.6% |
| 1.11 | nickel(II) chloride hexahydrate 100 mol% | 140° C. | 97.3% |

EXAMPLE 2

Procedure as described in Example 1, except that N,N-dimethylglycine is replaced by 134.1 mg (0.8 mmol) of 4-(dimethylamino)butyric acid hydrochloride.

TABLE 2

| Example No. | Metal additive [mol %], based on palladium used | Reaction temperature | Yield of Heck product in the reaction mixture |
|---|---|---|---|
| 2.1 | ---none--- | 135° C. | 92.9% |
| 2.2 | chromium(III) acetylacetonate 20 mol % | 135° C. | 95.0% |
| 2.3 | iron(II) acetate 20 mol % | 135° C. | 96.7% |
| 2.3 | iron(III) acetylacetonate 10 mol % | 135° C. | 96.9% |
| 2.4 | iron(III) chloride hexahydrate 10 mol % | 135° C. | 97.4% |
| 2.5 | iron(III) chloride hexahydrate 20 mol % | 135° C. | 97.7% |
| 2.6 | iron(III) chloride hexahydrate 200 mol % | 135° C. | 97.1% |
| 2.7 | nickel(II) chloride hexahydrate 20 mol % | 135° C. | 96.3% |

EXAMPLE 3

Procedure as described in Example 1, except that N,N-dimethylglycine was replaced by 140.2 mg (0.8 mmol) of 3-indolylacetic acid.

TABLE 3

| Example No. | Metal additive [mol %], based on palladium used | Reaction temperature | Yield of Heck product in the reaction mixture |
|---|---|---|---|
| 2.1 | ---none--- | 135° C. | 90.3% |
| 2.2 | chromium(III) acetylacetonate 20 mol % | 135° C. | 94.6% |
| 2.3 | iron(II) acetate 20 mol % | 135° C. | 97.0% |
| 2.3 | iron(III) acetylacetonate 10 mol % | 135° C. | 96.8% |
| 2.4 | iron(III) chloride hexahydrate 10 mol % | 135° C. | 97.0% |
| 2.5 | iron(III) chloride hexahydrate 20 mol % | 135° C. | 97.1% |
| 2.6 | iron(III) chloride hexahydrate 200 mol % | 135° C. | 96.7% |

TABLE 3-continued

| Example No. | Metal additive [mol %], based on palladium used | Reaction temperature | Yield of Heck product in the reaction mixture |
|---|---|---|---|
| 2.7 | nickel(II) chloride hexahydrate 20 mol % | 135° C. | 95.1% |

EXAMPLE 4

Comparative Example According to DE 198 43 012

63.20 g (0.1 mol) of 2,2',7,7'-tetrabromospirobifluorene, 0.898 g (0.004 mol) of palladium(II) acetate, 8.25 g (0.08 mol) of N,N-dimethylglycine, 201.62 g (2.4 mol) of sodium hydrogencarbonate and 108.15 g (0.60 mol) of 1,1-diphenylethene were weighed into a 2 l four-neck flask equipped with a precision glass stirrer, reflux condenser and internal thermometer, and admixed with 500 ml of N-methylpyrrolidinone. The suspension was degassed using nitrogen with stirring, while heating was effected to an internal temperature of 140° C. for one hour and this temperature was maintained for 18 h. After 18 hours, the mixture was allowed to cool to 70° C., 500 ml of toluene and 300 ml of water were added, and stirring was continued for 2 hours, the aqueous phase was removed and the organic phase was washed three times with 300 ml of water. The organic phase was stirred into 1500 ml of methanol. The precipitate which had precipitated out was filtered off with suction and dried.

The yield of the crude Heck product 2,2',7,7'-tetrakis(2,2'-diphenylvinyl)spiro-9,9'-bifluorene having a purity of 93.8-94.3% in 5 repetitions was in each case between 90-95 g (crude yield: 87-92%).

In each case, this crude product (depending on the batch) was recrystallized 10-15 times from dioxane until a purity of >99.9% had been achieved. The final yield of 2,2',7,7'-tetrakis (2,2'-diphenylvinyl)spiro-9,9'-bifluorene having a purity of >99.9% was between 25-35 g (pure yield: 24-34%).

EXAMPLE 5

The procedure was as described in Example 5, except that 20 mol % of the metal additive iron(III) chloride hexahydrate were added, based on the palladium(II) acetate used, corresponding to 0.216 g (0.0008 mol).

The yield of the crude Heck product 2,2',7,7'-tetrakis(2,2'-diphenylvinyl)spiro-9,9'-bifluorene having a purity of 98.0-98.4% in 5 repetitions was in each case between 95-100 g (crude yield: 92-97%).

In each case, the crude product (depending on the batch) was recrystallized 5-7 times from dioxane until a purity of >99.9% had been achieved. The final yield of 2,2',7,7'-tetrakis (2,2'-diphenylvinyl)spiro-9,9'-bifluorene having a purity of >99.9% was between 50-65 g (pure yield: 49-63%).

EXAMPLE 6

Comparative Example According to DE 198 43 012

29.60 g (0.1 mol) of 2,5-dibromo-1,4-bis(hydroxymethyl) benzene, 0.449 g (0.002 mol) of palladium(II) acetate, 4.13 g (0.04 mol) of N,N-dimethylglycine, 50.41 g (0.6 mol) of sodium hydrogencarbonate and 54.08 g (0.03 mol) of 1,1-diphenylethene were weighed into a 2 l four-neck flask equipped with a precision glass stirrer, a reflux condenser and an internal thermometer, and admixed with 250 ml of N-methylpyrrolidinone. The suspension was degassed using nitrogen with stirring, while heating was effected to an internal temperature of 140° C. for one hour and this temperature was maintained for 12 h. After 18 hours, the mixture was left to cool to 70° C., 500 ml of toluene and 500 ml of water were added, stirring was continued for 2 hours, filtration by suction from the precipitated, colorless solid was effected and this was washed three times with 200 ml of methanol.

The yield of the crude Heck product 2,5-bis(2,2'-diphenylvinyl)-1,4-bis(hydroxymethyl)benzene having a purity of 96.0-96.4% in three repeat batches was between 40-43 g (crude yield: 81-87%).

In each case, the crude product (depending on the batch) was recrystallized 7-9 times from dichloromethane/methanol (½ v/v) until a purity of >99.8% is achieved. The final yield of 2,5-bis(2,2'-diphenylvinyl)-1,4-bis(hydroxymethyl)benzene having a purity of >99.8% was between 20-25 g (pure yield: 40-51%).

EXAMPLE 7

The procedure was as described in Example 6, except that 10 mol % of the metal additive iron(III) chloride hexahydrate were added, based on the amount of palladium(II) acetate used, corresponding to 0.054 g (0.0002 mol).

The yield of the crude Heck product 2,5-bis(2,2'-diphenylvinyl)-1,4-bis(hydroxymethyl)benzene having a purity of 98.2-98.5% in 3 repeat batches was 44-47 g (crude yield: 89-95%).

In each case, the crude product (depending on the batch) was recrystallized 3-5 times from dichloromethane/methanol (½ v/v) until a purity of >99.8% had been achieved. The final yield of 2,5-bis(2,2'-diphenylvinyl)-1,4-bis(hydroxymethyl) benzene having a purity of >99.8% was between 38-43 g (pure yield: 77-87%).

EXAMPLE 8

Comparative Example According to DE 198 43 012

81.87 g (100 mmol) of 2,7-dibromo-2',3',6',7'-tetrakis(2-methylbutyloxy)spiro-9,9'-bifluorene, 0.225 g (1 mmol) of palladium(II) acetate, 2.07 g (20 mmol) of N,N-dimethylglycine, 25.2 g (0.3 mol) of sodium hydrogencarbonate and 31.65 g (100 mmol) of 1-(3,7-dimethyloctyloxy)-4-methoxy-2,5-divinylbenzene were weighed into a 2 l four-neck flask equipped with a precision glass stirrer, a reflux condenser and an internal thermometer, and admixed with 1000 ml of N-methylpyrrolidinone. The suspension was degassed using nitrogen with stirring, heated to an internal temperature of 140° C. over one hour and maintained at this temperature for 12 h. During this time, the viscosity of the solution increased distinctly. The batch was then cooled to 70° C. and added to 1000 ml of water. The yellow crude polymer which precipitated out was filtered off with suction, washed with methanol and dried in a vacuum drying cabinet (crude yield ~97 g, i.e. ~100%).

The purification was effected by dissolving twice in THF and precipitating out in methanol each time. The solutions used were 10% in each case.

The yield of poly[(2',3',6',7'-tetrakis(2-methylbutyloxy) spiro-9,9'-bifluoren-2,7-ylene-1,2-vinylene)-alt-({2-(3,7-dimethyloctyloxy)-5-methoxy-1,4-phenylene}-1,2-vinylene)] after these purification steps was 77.0 g (79%). The polymer has good solubility in solvents such as dichloromethane, THF and toluene, but in contrast is virtually insoluble in alcohols such as methanol and ethanol, and is a pulverulent yellow solid. GPC: THF+0.25% of oxalic acid; column set SDV500, SDV1000, SDV10000 (PSS), 35° C., RI detection, polystyrene standard: $M_w=6.5\times10^4$ g/mol, $M^n=2.9\times10^4$ g/mol (corresponds to a degree of polymerization DP≈30).

EXAMPLE 9

The procedure was as described in Example 8, except with the addition of 10 mol % of the metal additive iron(III) chloride hexahydrate, based on the amount of palladium(II) acetate used, corresponding to 0.027 g (0.1 mmol).

The workup was likewise effected similarly to Example 8, although when reprecipitating, it was possible only for 6% solutions in THF to be used owing to the higher viscosities.

Similarly to Example 8, the yield of polymer after these purification steps was 81.4 g (84%). The polymer is a fibrous yellow solid.

GPC: THF+0.25% of oxalic acid; column set SDV500, SDV1000, SDV10000 (PSS), 35° C., RI detection, polystyrene standard: $M_w=3.1\times10^5$ g/mol, $M_n=1.45\times10^5$ g/mol (corresponds to a degree of polymerization DP≈150).

What is claimed is:

1. A process for reacting a functional aryl or heteroaryl compound with an olefin derivative which has at least one hydrogen atom on the double bond in the presence of a simple palladium compound, optionally in the presence of a nitrogen additive, and of a base in a solvent, to form a C—C bond and formally cleave off the functional group of the aryl or heteroaryl derivative and a hydrogen atom of the olefin compound, wherein said functional group of said aryl or heteroaryl derivative is a reactive leaving group suitable for this reaction, characterized by the presence of at least one metal additive wherein the metal additive comprises at least one metal selected from the group consisting of iron, ruthenium, rhodium, osmium, iridium, and platinum, with the proviso that said metal additive does not comprise cobalt.

2. A process for reacting a functional aryl or heteroaryl compound with an olefin derivative which has at least one hydrogen atom on the double bond in the presence of a simple palladium compound and a nitrogen additive, and of a base in a solvent, to form a C—C bond and formally cleave off the functional group of the aryl or heteroaryl derivative and a hydrogen atom of the olefin compound, wherein said functional group of said aryl or heteroaryl derivative is a reactive leaving group suitable for this reaction, characterized by the presence of at least one metal additive wherein the metal additive comprises at least one metal selected from the group consisting of iron, cobalt, ruthenium, rhodium, osmium, iridium, and platinum.

3. The process as claimed in claim 2, wherein the nitrogen additive is an aminocarboxylic acid or an aminocarboxylic acid derivative.

4. The process as claimed in claim 2, wherein the nitrogen additive is dimethylglycine, 4-dimethylaminobutyric acid or 3-indolylacetic acid.

5. The process as claimed in claim 2, wherein the metal additive is a metal selected from the group consisting of iron, cobalt, ruthenium, rhodium, osmium, iridium, and platinum, an alloy containing any of these metals, a compound containing any of these metals, a salt containing any of these metals or chalcogenide containing any of these metals.

6. The process as claimed in claim 4, wherein the metal additive is a metal selected from the group consisting of iron, cobalt, ruthenium, rhodium, osmium, iridium, and platinum, an alloy containing any of these metals, a compound containing any of these metals, a salt containing any of these metals or chalcogenide containing any of these metals.

7. The process as claimed in claim 5, wherein the metal additive comprises at least one metal selected from iron, and cobalt.

8. The process as claimed in claim 6, wherein the metal additive comprises at least one metal selected from iron, and cobalt.

9. The process as claimed in claim 5, wherein the metal additive comprises iron.

10. The process as claimed in claim 5, wherein the metal additive is a halide, sulfate, acetate or other carboxylate.

11. The process as claimed in claim 5, wherein the metal additive used is an oxide or complex.

12. The process as claimed in claim 5, wherein the metal additive used is a metal alloy or metallic alloy.

13. The process as claimed in claim 9, wherein the iron additive used is an iron ore, forms of steel or cast iron.

14. The process as claimed in claim 1, wherein the multifunctional aryl or heteroaryl compounds and olefins which react monofunctionally are used.

15. The process as claimed in claim 1, wherein monofunctional aryl or heteroaryl compounds and olefins or compounds which have a plurality of monofunctional olefinic ends and react multifunctionally are used.

16. The process as claimed claim 1, wherein polymers are prepared by reacting bifunctional aryl or heteroaryl compounds with bifunctional olefin derivatives.

17. The process as claimed in claim 1, wherein 2,2',7,7'-tetrakis(2,2'-diphenylvinyl)spiro-9,9'-bifluorene is prepared by reacting 2,2',7,7'-tetrabromospiro-9,9'-bifluorene with 1,1-diphenylethene.

18. The process as claimed in claim 1, wherein said functional group of said aryl or heteroaryl derivative is a reactive functional group selected from the group consisting of chlorine, bromine, iodine, methylsulfonate, tosylate, triflate, nonaflate, and diazonium salt.

* * * * *